US012350027B2

(12) United States Patent
Verma

(10) Patent No.: US 12,350,027 B2
(45) Date of Patent: Jul. 8, 2025

(54) ERBIUM DOPED GLASS FOR OPTICAL AMPLIFICATION IN DETECTING A PHOTOPLETHYSMOGRAPHY

(71) Applicant: Google LLC, Mountain View, CA (US)

(72) Inventor: Yogesh Verma, Pleasanton, CA (US)

(73) Assignee: Google LLC, Mountain View, CA (US)

( * ) Notice: Subject to any disclaimer, the term of this patent is extended or adjusted under 35 U.S.C. 154(b) by 1021 days.

(21) Appl. No.: 17/296,118

(22) PCT Filed: May 22, 2020

(86) PCT No.: PCT/US2020/034292
§ 371 (c)(1),
(2) Date: May 21, 2021

(87) PCT Pub. No.: WO2021/236102
PCT Pub. Date: Nov. 25, 2021

(65) Prior Publication Data
US 2022/0087557 A1    Mar. 24, 2022

(51) Int. Cl.
*A61B 5/024*    (2006.01)
*A61B 5/00*    (2006.01)
(Continued)

(52) U.S. Cl.
CPC ........ *A61B 5/02427* (2013.01); *A61B 5/0205* (2013.01); *A61B 5/02438* (2013.01);
(Continued)

(58) Field of Classification Search
CPC ............ A61B 5/14552; A61B 5/02427; A61B 5/0205; A61B 5/02438; A61B 5/7264
See application file for complete search history.

(56) References Cited

U.S. PATENT DOCUMENTS

| 5,629,953 A | 5/1997 | Bishop et al. |
| 2010/0049017 A1 | 2/2010 | LeBoeuf et al. |

(Continued)

FOREIGN PATENT DOCUMENTS

| CN | 101404935 A | 4/2009 |
| CN | 104073676 A | 10/2014 |

(Continued)

OTHER PUBLICATIONS

Office Action for Japanese Patent Application No. 2023-072260 dated Mar. 5, 2024. 5 pages.

(Continued)

*Primary Examiner* — Eric F Winakur
(74) *Attorney, Agent, or Firm* — Lerner David LLP

(57) ABSTRACT

A user device for monitoring a physical condition of a user, such as a heart rate or blood oxygen level, includes an erbium doped glass component and a light source. The light source is configured to generate light equal to an excitation frequency of the erbium doped glass. The erbium doped glass component is configured to generate, through photoluminescence, one or more peaks of higher intensity light corresponding to a wavelength which can be used to monitor a physical condition of a user. The amplified light is sent to the user and received back at a photodetector, which can then algorithmically determine a physical condition of a user.

20 Claims, 7 Drawing Sheets

(51) Int. Cl.
  *A61B 5/0205* (2006.01)
  *A61B 5/1455* (2006.01)
  *C03C 3/16* (2006.01)
  *C03C 4/12* (2006.01)

(52) U.S. Cl.
  CPC ........ *A61B 5/14552* (2013.01); *A61B 5/7264* (2013.01); *C03C 3/16* (2013.01); *C03C 4/12* (2013.01); *C03C 2204/00* (2013.01)

(56) References Cited

U.S. PATENT DOCUMENTS

| | | | |
|---|---|---|---|
| 2015/0305658 A1* | 10/2015 | Islam | A61B 5/14532 600/322 |
| 2015/0353419 A1 | 12/2015 | Jose et al. | |
| 2016/0310049 A1 | 10/2016 | Rowe et al. | |
| 2017/0014037 A1 | 1/2017 | Coppola et al. | |
| 2017/0156650 A1* | 6/2017 | Bower | A61B 5/14552 |
| 2020/0193121 A1 | 6/2020 | Bourquin | |

FOREIGN PATENT DOCUMENTS

| | | |
|---|---|---|
| CN | 104093676 A | 10/2014 |
| CN | 107371361 A | 11/2017 |
| CN | 109952057 A | 6/2019 |
| JP | H04349141 A | 12/1992 |
| JP | H05261106 A | 10/1993 |
| JP | 2017512581 A | 5/2017 |
| JP | 2017173899 A | 9/2017 |
| JP | 2019533509 A | 11/2019 |
| JP | 2020004126 A | 1/2020 |
| WO | 2018083351 A1 | 5/2018 |

OTHER PUBLICATIONS

Office Action for Taiwanese Patent Application No. 110118398 dated May 22, 2024. 15 pages.
Office Action for Japanese Patent Application No. 2023-072260 dated Jul. 9, 2024. 3 pages.
International Preliminary Report on Patentability for International Application No. PCT/US2020/034292 dated Dec. 1, 2022. 12 pages.
Office Action for Japanese Patent Application No. 2021-529029 dated Dec. 20, 2022. 4 pages.
Office Action for Taiwanese Patent Application No. 110118398 dated Feb. 14, 2023. 12 pages.
International Search Report and Written Opinion for International Application No. PCT/US2020/034292 dated Dec. 21, 2020. 17 pages.
First Office Action for Chinese Patent Application No. 202210070954.4 dated Mar. 28, 2024. 12 pages.
Office Action for Japanese Patent Application No. 2021-529029 dated Oct. 4, 2022. 4 pages.
Office Action for Taiwanese Patent Application No. 110118398 dated Oct. 5, 2023. 4 pages.
Office Action for European Patent Application No. 20732708.1 dated Oct. 6, 2023. 8 pages.
Office Action for Taiwanese Patent Application No. 110118398 dated Oct. 28, 2024. 15 pages.
Office Action for Chinese Patent Application No. 202080006268.X dated Oct. 24, 2024. 10 pages.
Office Action for Japanese Patent Application No. 2023-072260 dated Dec. 24, 2024. 3 pages.
Office Action for Chinese Patent Application No. 202080006268.X dated Apr. 11, 2025. 7 pages.

* cited by examiner

Method 500

ERBIUM DOPED GLASS FOR OPTICAL AMPLIFICATION IN DETECTING A PHOTOPLETHYSMOGRAPHY

CROSS-REFERENCE TO RELATED APPLICATIONS

The present application is a national phase entry under 35 U.S.C. § 371 of International Application No. PCT/US2020/034292 filed May 22, 2020.

BACKGROUND

Photoplethysmography (PPG) is an optical measurement method which measures changes in the volume of a tissue and requires a light source and a photodetector. A photodetector, typically placed at or close to the surface of skin, detects light which is either transmitted or reflected from vascular tissue to the photodetector. This light corresponds to measuring variations in the volume of blood circulation, which is used to monitor heart rate. The change in volume caused by a pulse or cardiac cycle can be measured as a peak or trough in the intensity of light. The technique can also be used to measure other aspects related to blood flow, such as oxygen saturation level of the blood. The PPG technique is used in personal consumer devices, such as for example, smartphones or smartwatches, to measure the heartbeat of a consumer.

The reliability and efficacy of the PPG technique depends on using wavelengths of light which are suitable for penetrating the skin and vascular tissue. Not all wavelengths of light are equally absorbed in blood. For example, a wavelength corresponding to green light shows the strongest absorption in blood and gives the highest pulsatile signal intensity corresponding to the heart beat. In actual implementation of PPG, LEDs corresponding to various wavelengths of light are used. A green LED is used to detect the heartbeat. An infrared (IR) LED is used to detect heart beat during sleep and a red LED is used to detect oxygen saturation levels. Each LED has a different efficiency when it comes to consuming power. Green LED consumes a higher amount of power to output light of a certain luminosity while IR led consumes a fraction of the power to output the same luminosity.

SUMMARY

The present disclosure provides erbium doped glass for optical amplification for use in photoplethysmography.

One aspect of the present disclosure provides a device including a first light source configured to generate light with a first wavelength and first intensity, an amplification layer further comprising a doped rare earth metal and with a first side and a second side, the amplification layer configured to receive light of the first wavelength and first intensity and transmit light of a second wavelength with a second intensity, a photodetector receiving light of the second wavelength from a user, a processor configured to determine a physical condition of a user based on at least a signal received from the photodetector. The first wavelength can be an excitation frequency of the amplification layer and the second intensity can be higher than the first intensity.

Additional aspects of this disclosure provide a device including a first light source configured to generate light with a first wavelength and first intensity, an amplification layer further comprising a doped rare earth metal and with a first side and a second side, the amplification layer configured to receive light of the first wavelength and first intensity and transmit light of a second wavelength with a second intensity, a photodetector receiving light of the second wavelength from a user, a processor configured to determine a physical condition of a user based on at least a signal received from the photodetector. The first wavelength can be an excitation frequency of the amplification layer and the second intensity can be higher than the first intensity. The amplification layer can also transmit light of a third wavelength and the photodetector can receive light of the third wavelength. The processor can be configured to monitor a blood oxygen level based on the light of the second wavelength and/or the processor can also be configured to monitor a heart condition based on light of the third wavelength. The photodetector can generate electrical signals responsive to the light it receives. The device can comprise a processor electrically coupled to the photodetector. The processor can be configured to evaluate a health state of a user based on the received photons of the second wavelength. The device can also comprise a paint which blocks the visible light spectrum. The paint can be on either the first side or the second side of the amplification layer. The first wavelength can be within the infra-red spectrum. The first amplification layer can be made from erbium doped phosphate glass. The first amplification layer can be erbium doped phosphate glass with between 0.4 mole percent and 0.6 mole percent of erbium. The second wavelength can be from the range of 550 to 750 nm wavelength.

Additional aspects of this disclosure provide monitoring a physical parameter of a user including providing an amplification layer, the amplification layer configured to have a first excitation wavelength and generate a second excitation wavelength, generating by a light source light of a first wavelength, the first wavelength corresponding to the first excitation wavelength, receiving the light of a first wavelength at the amplification layer, generating light of a second wavelength at the amplification layer responsive to the received light of a first wavelength, transmitting the light of a second wavelength from the amplification layer to the user, receiving from the user and at a photodetector, the light of a second wavelength and evaluating by a processor a health condition of a first user based on at least the light of a second wavelength received at the photodetector.

Additional aspects of this disclosure provide monitoring a physical parameter of a user including providing an amplification layer, the amplification layer configured to have a first excitation wavelength and generate a second excitation wavelength, generating by a light source light of a first wavelength, the first wavelength corresponding to the first excitation wavelength, receiving the light of a first wavelength at the amplification layer, generating light of a second wavelength at the amplification layer responsive to the received light of a first wavelength, transmitting the light of a second wavelength from the amplification layer to the user, receiving from the user and at a photodetector, the light of a second wavelength and evaluating by a processor a health condition of a first user based on at least the light of a second wavelength received at the photodetector. The physical parameter can be a user's heart rate. The physical parameter can be the user's blood oxygen level. The amplification layer can be configured to generate light of a third wavelength. The second wavelength can correspond to red light and the third wavelength can correspond to green light. Evaluation by a processor can comprise execution of a machine learning algorithm to evaluate an additional underlying health condition of a user.

Additional aspects of this disclosure provide a device including a housing, a first light source, an amplification layer, a photodetector, and a processor. The housing can comprise a back portion adapted to be placed adjacent to a user's skin and the back portion can be at least partially comprised of a glass and the glass can be doped with a rare earth metal. The first light source can be configured to generate light with a first wavelength and a first intensity. The amplification layer can be doped with a rare earth metal. The amplification layer can contain a first side and a second side, and be configured to receive light of a first wavelength and a first intensity and transmit light of a second wavelength and second intensity. The photodetector can receive light of the second wavelength from a user. The processor can be configured to determine a physical condition of a user based on at least a signal received from a photodetector. The first wavelength can be an excitation frequency of the amplification layer and the second intensity can be higher than the first intensity. The rare earth metal can be erbium. The glass can be at least partially painted with an ink to block the visible light spectrum.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

This disclosure generally relates to methods, systems, and apparatuses which use erbium doped glasses as an optical amplifier and wavelength shifter. In particular, rare earth metals exhibit photoluminescence. Photoluminescence is a phenomenon in which light is absorbed by a material at one wavelength and re-emitted at a different wavelength. In particular, the use of doped materials can downconvert and amplify wavelengths of light which are suitable for particular optimal purposes, such as photoplethysmography (PPG). The use of doped materials, such as erbium doped glass, can amplify light and improve the power consumption efficiency or characteristics of a device. Various levels of doping can exist for erbium doped glass, which can be measured by weight of materials, weight percentage, volume percentage, or mole percentage. Mole percent is the percentage of the total moles that is of a particular component, and can be annotated "mole %." It is to be understood that Erbium as used in this disclosure refers to both erbium and erbium compounds, such as erbium oxide $Er_2O_3$.

Photoluminescence is re-emission of light from any form of matter after the absorption of photons, light or electromagnetic radiation. In certain materials, such as rare-earth ions and rare-earth ion doped glasses, the intensity or lumens of light emitted by a photoluminescent material is higher than the intensity which was absorbed.

Erbium doped glass can be of a class of sodium sulfo-phosphate glasses. Doped glasses and other materials have been discovered which exhibit strong photoluminescent effects. Spectral analysis of such materials has revealed that, in particular, with 977 nm excitation, NPbPEr-0.5 glass emits enhanced green emission. Other doped glasses can also exhibit similar behavior.

Figure 1:
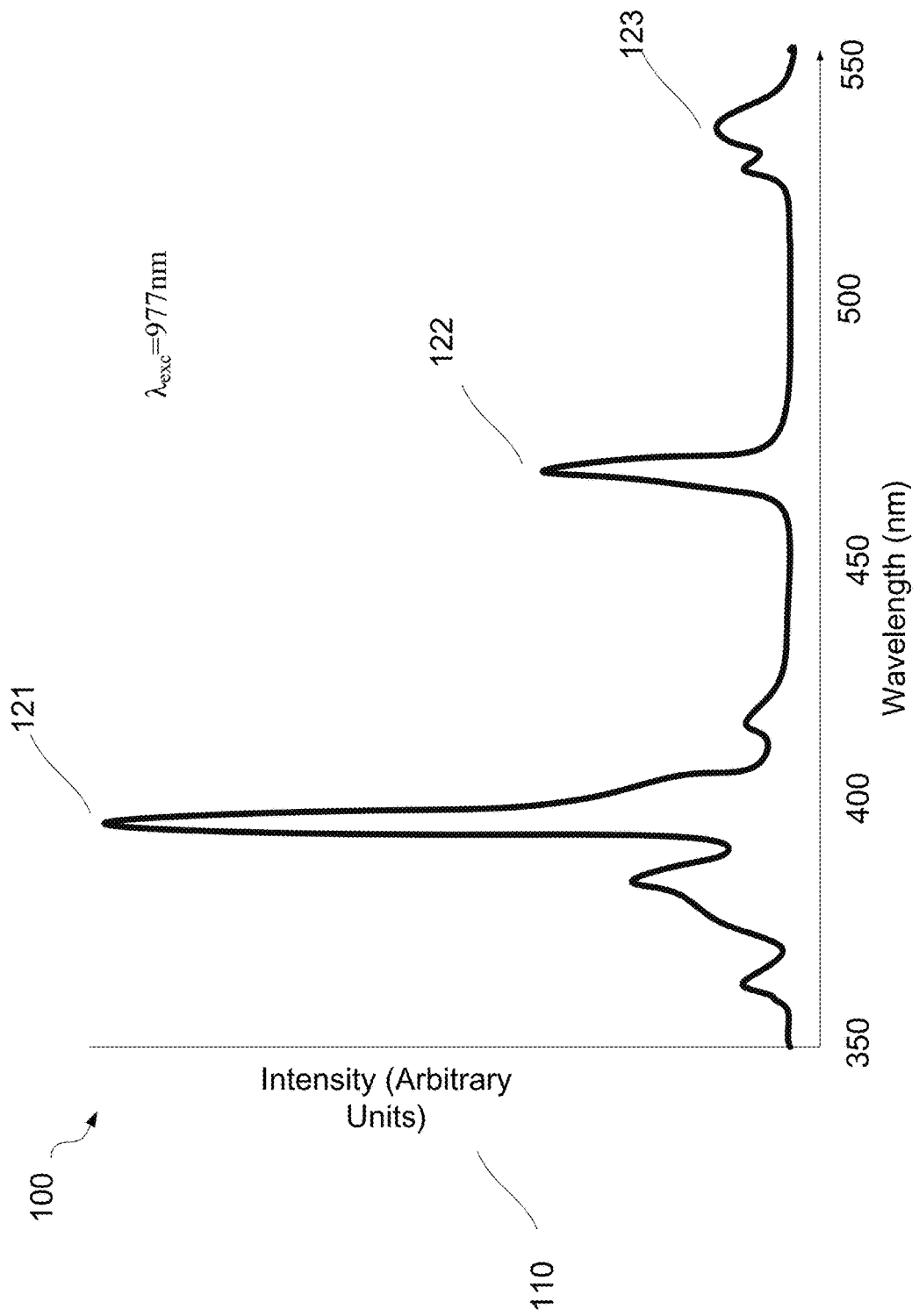
FIG. 1 is a graph of wavelength and intensity of example erbium doped glass plates according to aspects of the disclosure.

FIG. 1 illustrates a graph 100 of wavelength and intensity or luminous intensity for light emitted from an erbium doped glass when exposed to light of a particular wavelength, labeled $\lambda_{exc}$. The excitation wavelength may be an ultraviolet, visible, or infrared wavelength of light. The physical phenomenon in which a material is exposed to such a wavelength of light and re-emits light of a different wavelength is known as photoluminescence. An erbium doped glass absorbs the light to which it is exposed and emits light of different wavelengths and intensities. The horizontal axis 105 indicates the wavelength of light that is being emitted, measured in units of nanometers (nm). The vertical axis 110, indicates the intensity of light emitted in arbitrary units. Also shown on graph 100 are several peaks 121-123. These are peaks of intensity at different wavelengths, such as peak 121 near roughly 400 nm, peak 122 near 475 nm, and peak 123 near roughly 540 nm. Other smaller peaks can be seen on graph 100 which are not labeled. Through the process of photoluminescence, the amplitude of light emitted has a larger amplitude or intensity than the amplitude of light which excites the erbium doped glass at particular wavelengths. The peaks correspond to particular excitations and emissions which occur when an electron is excited by a photon of a certain wavelength to jump between two electron orbital states and then falls back into a different orbital state thereby releasing a photon of a different wavelength.

The erbium doped glass can be formed or synthesized by melt quench (rapid cooling) methods. After choosing a specific molar composition for the glass, such as a composition of (20-x) $Na_2SO_4$-20PbO-60$P_2O_5$-$xEr_2O_3$ (x=0.1, 0.3, 0.5, 0.7, 1.0 mol %), the materials can be melted and poured into a mold, annealed, and gradually brought to an ambient temperature. X is a variable which can be adjusted for in the prior composition depending on the molar concentration of $Er_2O_3$.

Figure 2:
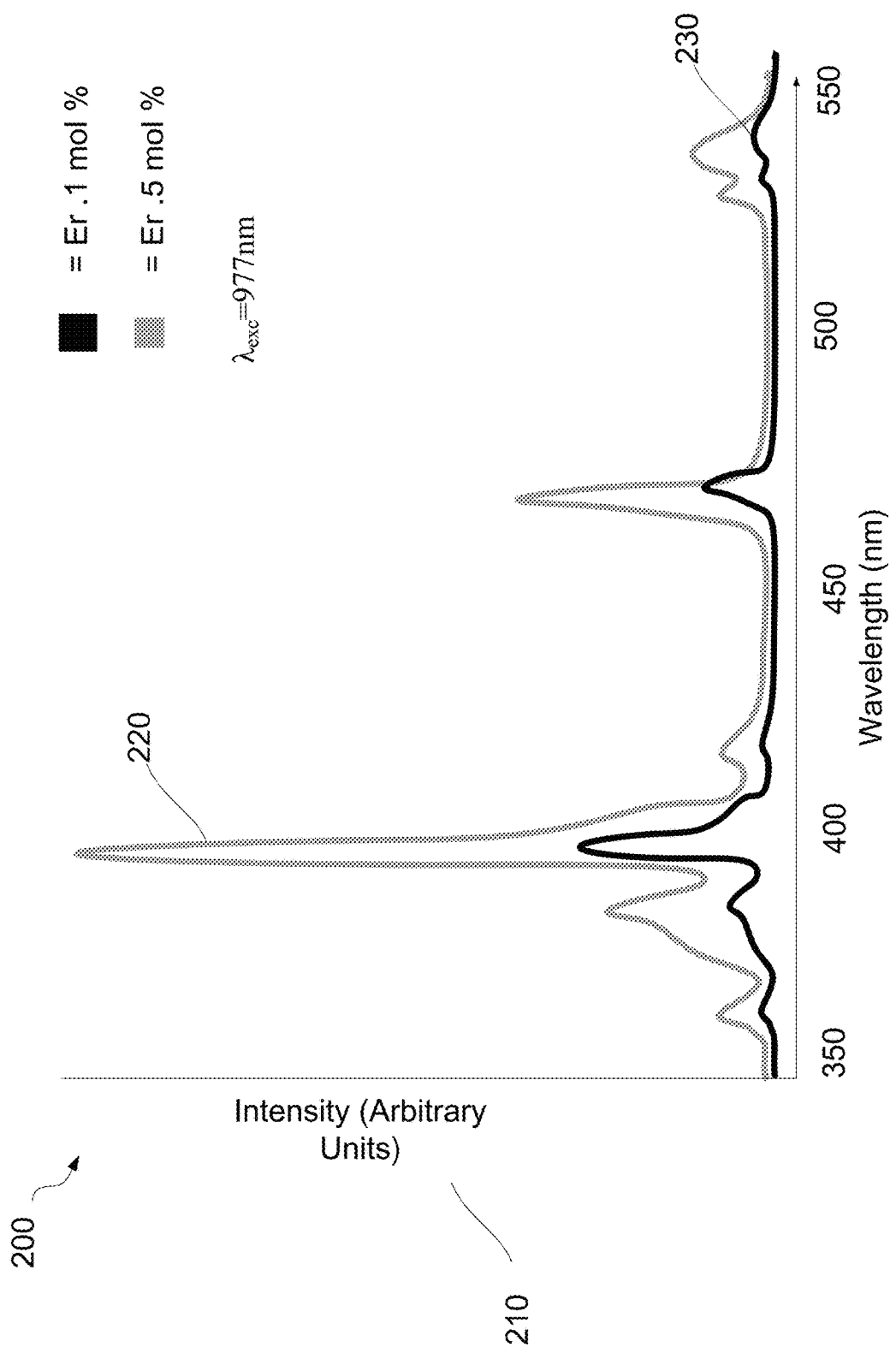
FIG. 2 is a graph of wavelength and intensity of example erbium doped glass plates according to aspects of the disclosure.

FIG. 2 illustrates a graph 200 of wavelength and intensity of two erbium doped glasses when exposed to light of a particular wavelength $\lambda_{exc}$. Similar to the example of FIG. 1 above, the excitation wavelength may be an ultraviolet, visible, or infrared wavelength of light. Two excitation curves, curve 220 and curve 230 are illustrated. Curve 220 corresponds to erbium doped glass where erbium makes up 0.5 mole % of the glass. Curve 230 corresponds to erbium doped glass where the erbium makes up 0.1 mole % of the glass. Curve 220 and curve 230 generally share characteristics, such as location of peaks, but the graphs reflect different amplitudes of the light generated by the photoluminescence effect. The "doping percentage" or amount of erbium, or other doping material used, leads to different curves for different levels of doped materials. In some examples, the glass may be doped to an extent which optimizes the height of the various excitation peaks illustrated in graph 200. In other examples, the glass may be doped such that the light generated by the photoluminescent effect is of a particular wavelength. Although two graphs have been illustrated for specific mole percentages, it is to be understood that other curves can be empirically derived for other mole percentages, and a curve most suitable for specific applications selected. As can be seen from FIG. 2, "Er-0.5" provides the strongest effect at roughly the 550 nm range, corresponding to green light, and roughly the 640-680 nm range, corresponding to red light. As can be seen from FIG. 2, the doped glass generates green light which is 100 to 1000 times the magnitude of the amplitude of the infrared signal used to excite the doped glass.

FIG. 3 illustrates a user device, 300, which can be used by a user, such as user 399. The user device can include a housing 301, and a strap 302. Housing 301 can have components such as a back portion, which will contact with the skin of user 399. The back portion can contain a glass portion which will allow light to pass through the back portion. For example, light can be generated from other components contained within housing 301, such as a light source. User device 300 and housing 301 can also have a user interface which allows user 399 to interact and view information from user device 300. The user interface can be part of a touchscreen or other device. Additional components which can be included in user device 300 or in housing 301 are further described below with reference to FIGS. 4A and 4B. The housing can further be of an appropriate thickness to include the components described in FIGS. 4A and 4B. Strap 302 can be a strap to hold the user device on a user, such as one made from metal, leather, cloth, or other material. For example, user device 300 can be a smartwatch, a health sensor, an earplug, earbuds, over-ear headphone, in-ear headphone, or other wearable, a ring, an anklet, necklace, or other piece of jewelry.

Figure 3A:
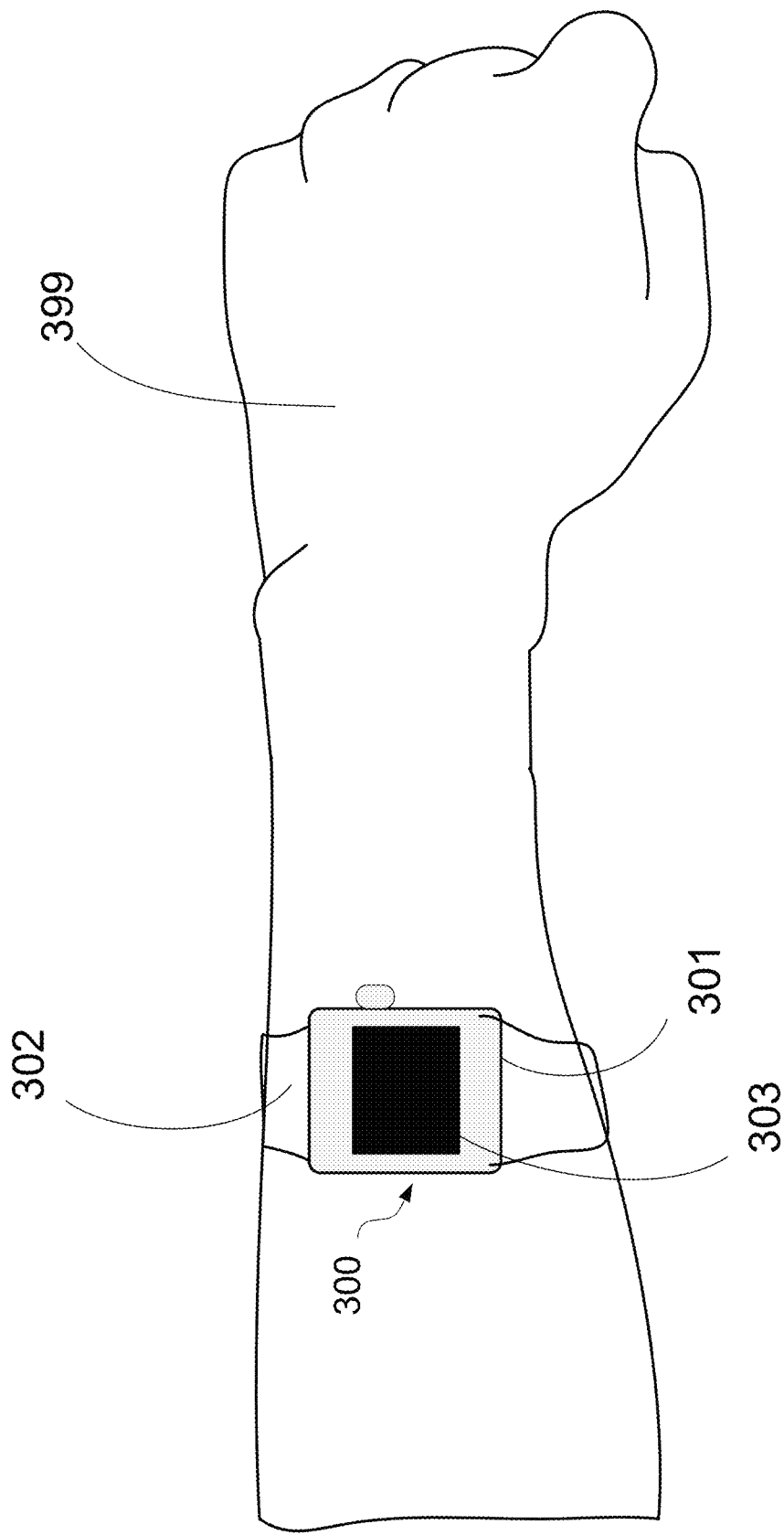
FIG. 3A is a diagram of a user device according to aspects of this disclosure.
Figure 3C:
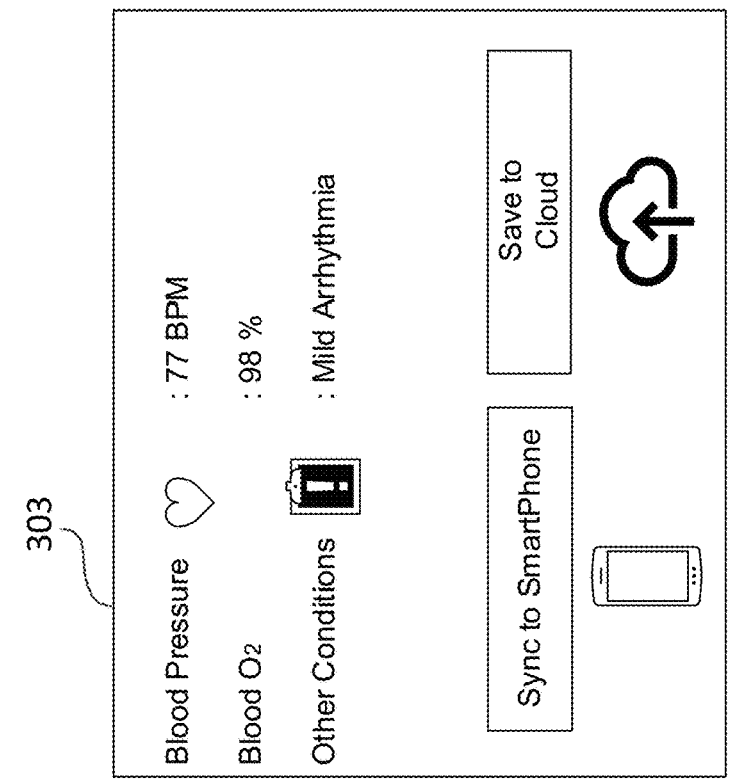
FIG. 3C is a diagram of user interfaces according to aspects of this disclosure.
Figure 3B:
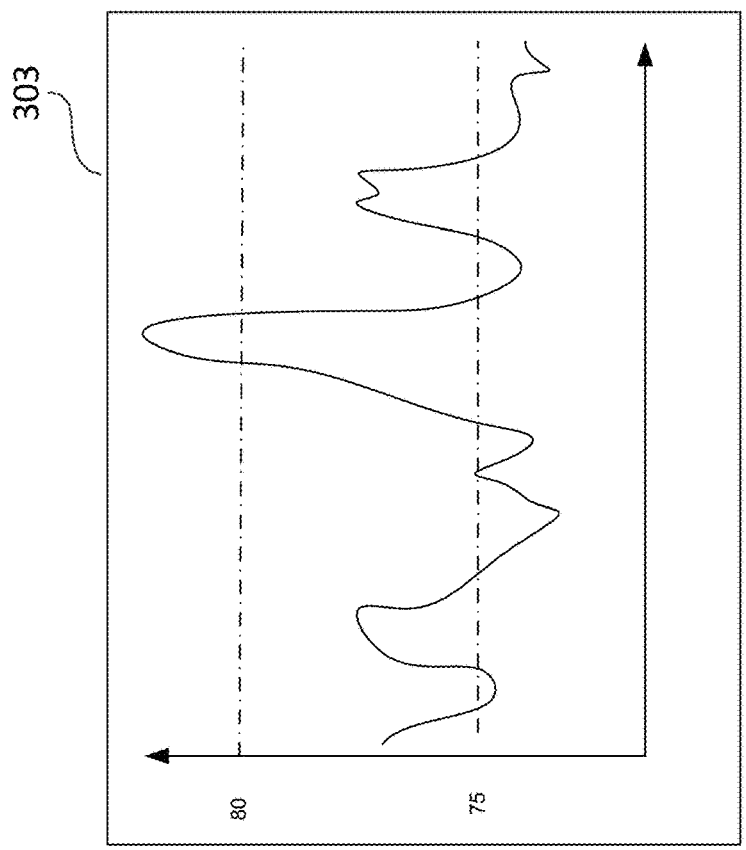
FIG. 3B is a diagram of user interfaces according to aspects of this disclosure.

FIG. 3B and FIG. 3C illustrate various example formats of displaying information about a physical condition of a user on a display 303. Display 303 can be similar to display 495 described below. For example, FIG. 3A illustrates information obtained through aspects of this disclosure, such as method 500, in a graphical format. FIG. 3B illustrates a graph of the current heart rate of a user of a device, such as device 400. This graphical view can be updated in real time to display a trailing number of seconds of the heartbeat of the user. In some examples, the information can be communicated to a user through a visual or auditory method. FIG. 3C illustrates displaying information about a physical condition of a user in a textual format. For example, FIG. 3B illustrates the current heart rate in beats-per-minute (BPM), the current blood oxygen saturation level, and any other conditions that may be of value to the user, such as an arrhythmia. Although the examples given are for cardiovascular conditions, other aspects of the heart can be monitored. FIG. 3C also illustrates other options, such as the ability to sync the information to another user device, such as a smartphone, or saving the information to another storage unit, such as the internet or to the cloud.

Figure 4A:
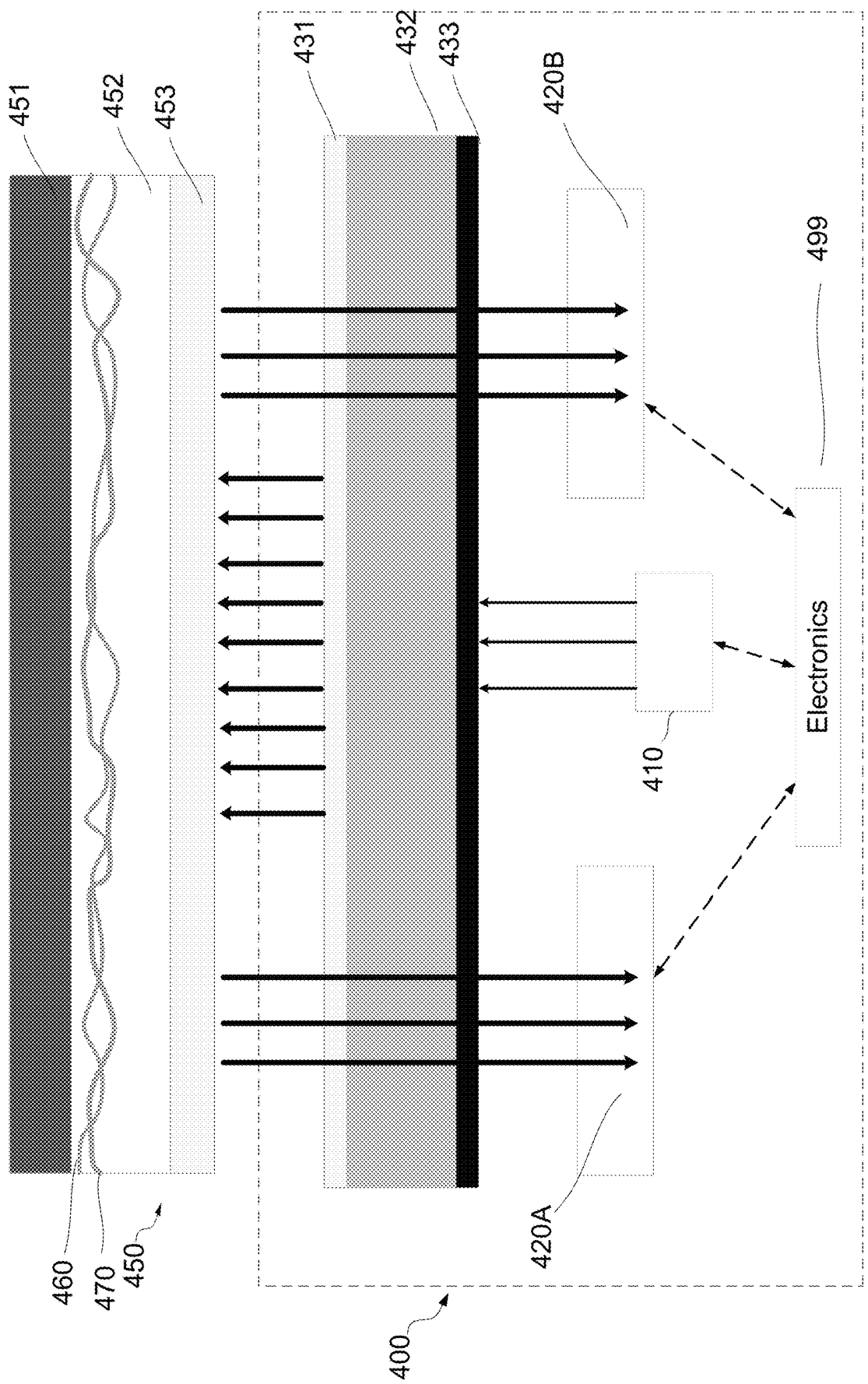
FIG. 4A is a diagram of a device with an erbium doped glass plate according to aspects of this disclosure.

FIG. 4A illustrates a device which can be used to perform PPG, device 400. Device 400 can comprise a light source, such as light source 410, one or more light sensors capable of detecting light, such as photodetectors 420A and 420B, an inked layer capable of allowing infra-red light to be transmitted, such as layer 433, a layer of glass to amplify light received from light source 410, such as amplification layer 432, and a protective layer of glass, such as back glass 431, and electronics 499. Electronics 499 may be some or all of the features of electronics 499 described below with reference to FIG. 4B. Light is illustrated with unlabeled solid arrows in FIG. 4, with the arrow indicating the direction in which the light travels. The light can be incident on a dermis, such as skin 450. Although skin 450 is shown, it is possible that the device is applied to other parts of a human body, such as for example, a nail or soft tissue. Layers 431-433 can respectively have a first side and a second side, and can be arranged in different permutations with respect to the light source.

FIG. 4A illustrates a light source 410. One example of a light source is a light-emitting diode (LED). An LED is a semiconductor light source which emits light responsive to electricity flowing through it. Electrons in the semiconductor recombine with electron holes, releasing energy in the form of photons. LEDs can be engineered or chosen to emit light at a particular wavelength or range of wavelengths. In other examples, light source 410 can be made of any commercially available source of light, such as specially designed semiconductors, incandescent light, electrodeless lamps, or halogen lamps. In other examples, light source 310 can further be made of one or more light sources configured to generate light of different wavelengths, such as an LED configured to generate red light which is close to a wavelength of 660 nm, an LED configured to generated green light which is close to a wavelength of 530 nm. These different light sources may be chosen to measure different aspects of a cardiovascular system when performing PPG. For example, green light may provide information regarding a heartbeat while red light may provide information about blood oxygen saturation, due to the relative absorption and reflection of these colors within the cardiovascular system. Light source 410 can be configured or chosen to generate light corresponding to the excitation wavelength of amplification layer 432. For example, infrared light at 977 nm can be chosen. The use of infrared light is more energy efficient when compared to the generation of other higher frequency/lower wavelength light. This is because infrared light can be generated using less electricity and be generated from a singular source while still causing light of more than one wavelength to be generated through photoluminescence. As explained further below, the light source can be amplified by amplification layer 432 before reaching skin 450.

A photodetector, such as photodetector 420A or 420B, can be a semiconductor device that converts light into an electrical current. The photodetector can generate a current which is proportional to the number of photons hitting the surface. As electricity is generated when photons are absorbed in the photodetector, the photodetector can act as a sensor for light. The photodetector can be any device which is capable of sensing intensities and/or wavelengths of light. Photodetectors 420A and 420B can be a photodiode or a photosensor. In some examples, photodetectors 420A and 420B can be chosen to be more sensitive to specific wavelengths of light. In some examples, photodetector 420A can be chosen or configured to be more sensitive or only sensitive to green light while photodetector 420B can be configured to be more sensitive or only sensitive to red light. Photodetectors 420A and 420B can also be made of an array of photodetectors. Additional circuitry, calibration, or electronics can be incorporated into the photodetectors or electronics 499 to ensure a better signal to noise ratio and reduce the effect of ambient light.

Also illustrated in FIG. 4A is skin 450, with a hypodermis layer 451, a dermis layer 452, and an epidermis layer 453. Epidermis layer 453 is a thinner layer of skin and can permit light to pass through it. The skin contains veins and arteries, such as vein 460 and artery 470. Light generated from light source 410 can be emitted from device 400 to skin 450. The light emitted can travel through the epidermis layer 453, the dermis layer 452, and be reflected from the veins and arteries within the skin, such as vein 460 or artery 470, and then be reflected back to photodetectors 420A or 420B. Light that hits skin 450 reflects off the various layers within the skin depending on the incident angle of the light. The light that hits the skin at shallow angles reflects off the top layer or epidermis layer 453. This reflected light contains little or no heartbeat information as it does not interact with arteries. Light that hits the skin at steeper angles penetrates the top layer of the skin to enter into other layers, such as the hypodermis layer 451 or the dermis layer 452, which contain a strong concentration of veins and arteries that carry blood, such as vein 460 and artery 470. Light that reflects off these layers carries the heartbeat signal and is useful for the purpose of PPG. Various components, such as the amplification layer described herein, can be formed to improve the angle at which light is incident to skin 450 to improve the information or signal received. Variations in the light transmitted to the photodetector can be used to determine various aspects of a cardiovascular system, such as the heart rate, pulse, oxygen saturation in the blood, or other health-related information. In some examples, a wave form can be derived from the continuous or near-continuous monitoring of light received by photodetector 420A. Light source 410 and photodetectors 420A and 420B can be connected with electronics 499 to control the emission of light, and to monitor and analyze the light received from skin 450.

Glass layer 431 can be a layer of glass which allows for light to pass through and cases the other components of device 400. Glass layer 431 can be formed from a silicate glass, such as soda-lime glass, lead glass, aluminosilicate glass, or be formed from a silica-free glass, such as an amorphous metal or a polymer glass. Molecular liquids or molten salts can also be used to make up glass layer 431. Glass layer 431 can be hardened or tempered to provide additional durability and resistance to scratching, cracking, or shattering. In other examples, commercially available glasses which have been chemically strengthened can be used, such as alkali-aluminosilicate.

Amplification layer 432 can be made of a rare-earth metal doped glass. In some examples, the rare earth metal can be erbium Amplification layer 432 receives light of a specific excitation wavelength and intensity, and re-emits, through the process of photoluminescence, light of a higher intensity at other wavelengths. For example, referring back to FIG. 2, glass which has been doped to maximize the amplitude of emitted light can be chosen to make up amplification layer 432. In other examples, the amplification layer 432 can be made from one or more optical glass fibers which have been doped. In yet other examples, it is possible that the amplification layer 432 is made of more than one type of doped glass, which would allow for more flexibility in engineering devices or for applications requiring more than one strong emission peak. As erbium doped glass can be formed in any shape or configuration, the amplification layer can also be shaped to match any use case. In some examples, the glass may be more curved to ensure better incidence of light onto skin 450. In some the erbium doped glass can be formed as an optical fiber. In some examples, the amplification layer can be coated with a reflective surface on some sides to further direct light to be emitted from only one portion. In other examples, optical fibers can be embedded into the amplification layer 432 to direct light towards skin 450. In other examples, the geometry of the amplification layer 432 can ensure that the amplified light is spread more with uniform flux at the surface of the amplification layer.

Layer 433 can be a layer which selectively allows certain wavelengths of light to pass through it while blocking other wavelengths of light. In some examples, layer 433 allows infrared light to pass through but prevents light of other wavelengths from being transmitted. For example, layer 433 can be made of glass in which the glass is inked with an infrared transparent ink. Layer 433 can extend along the length of amplification layer 432 or glass layer 431. In other examples, layer 433 can only extend over the portion of glass layer 431 through which light source 410 or photodetectors 420A may be visible. Thus, when incorporated into a user device, the internal components can be made invisible to a user without affecting the usability of device 400. The infrared transparent ink can be chosen from commercially available paints or be specifically fabricated from materials blocking light other than infrared light.

Although layers 431-433 are illustrated as continuous, rectangular, and adjacent layers, it is to be understood that variations of the placement, size, geometry, continuity of the layers is possible. For example, the layers can be curved to enable them to fit into a smartwatch or other device, such as device 300. In some examples, the layers can follow the curvature of a human wrist or other body part to better enable the layers to be incorporated into a device or housing which mimics the wrist. In other examples, the layers can be formed to fit around a molding, such as a camera lens of a smartphone. In some examples, additional layers can be inserted intra-layer or interlayer to provide additional structural rigidity, amplification, heat dissipation, or toughness. In other examples, a vacuum can exist in between the layers to increase bonding force between the layers or allow additional space for thermal expansion and contraction. In some examples, multiple layers can be used, which can be arranged in different permutations from one end of device 400 to the other end of the device. Additionally, other components, such as optical filters can be included surrounding the layers or in between the layers. In some examples, the optical filters can correspond to light which is not used to monitor a physical condition of a user.

Figure 4B:
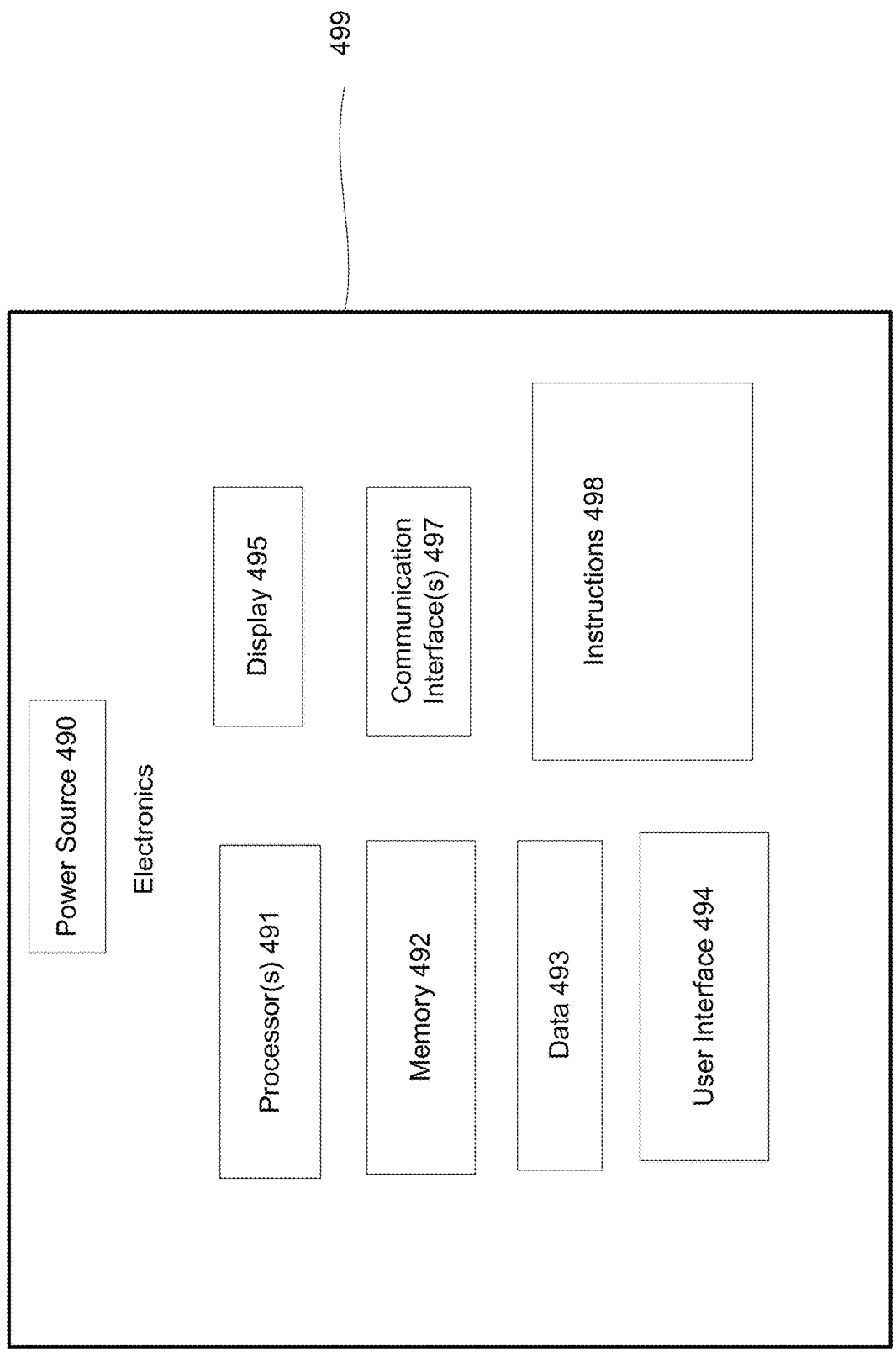
FIG. 4B is a diagram of a device with an erbium doped glass plate according to aspects of this disclosure.

It is to be understood that although device 400 is illustrated with a specific configuration, other arrangements of these components are within the scope of this disclosure. For instance, in some examples, these components can be arranged in user devices, such as a mechanical watch, a smart watch, a smart ring, a cell phone, earbud, headphone, armband, or a laptop computer. In other examples, device 400 can be integrated into jewelry, such as a pendant, necklace, bangle, earring, armband, ring, anklet, or other jewelry. In yet other examples, device 400 and/or its components can be integrated into medical devices, such as a pump-based blood pressure machine FIG. 4B illustrates additional aspects of electronics 499. Electronics 499 may contain a power source 490, processor(s) 491, memory 492, data 493, a user interface 494, a display 495, communication interface(s) 497, and instructions 498. The power source may be any suitable power source to generate electricity, such as a battery, a chemical cell, a capacitor, a solar panel, or an inductive charger. Processor(s) 491 may be any conventional processors, such as commercially available microprocessors or application-specific integrated circuits (ASICs); memory, which may store information that is accessible by the processors including instructions that may be executed by the processors, and data. Memory 492 may be of a type of memory operative to store information accessible by the processors, including a non-transitory computer-readable medium, or other medium that stores data that may be read with the aid of an electronic device, such as a hard-drive, memory card, read-only memory ("ROM"), random access memory ("RAM"), optical disks, as well as other write-capable and read-only memories. The subject matter disclosed herein may include different combinations of the foregoing, whereby different portions of the instructions and data are stored on different types of media. Data 493 of electronics 499 may be retrieved, stored or modified by the processors in accordance with the instructions 498. For instance, although the present disclosure is not limited by a particular data structure, data 493 may be stored in computer registers, in a relational database as a table having a plurality of different fields and records, XML documents, or flat files. Data 493 may also be formatted in a computer-readable format such as, but not limited to, binary values, ASCII or Unicode. Moreover, data 493 may comprise information sufficient to identify the relevant information, such as numbers, descriptive text, proprietary codes, pointers, references to data stored in other memories (including other network locations) or information that is used by a function to calculate the relevant data.

Instructions 498 may control various components and functions of device 400. For example, instructions 498 may be executed to selectively activate light source 410 or process information obtained by photodetector 420. In some examples, algorithms can be included as a subset of or otherwise as part of instructions 498 included in electronics 499. Instructions 498 can include algorithms to interpret or process information received, such as information received through or generated by analyzing a ray received at a photodetector, or information stored in memory. For example, physical parameters of the user can be extracted or analyzed through algorithms. Without limitation the algorithms could use any or all information about the waveform, such as shape, frequency, or period of a wave, Fourier analysis of the signal, harmonic analysis, pulse width, pulse area, peak to peak interval, pulse interval, intensity or amount of light received by a photodetector, wavelength shift, first or second derivatives of the signal generated or received by photodetector 420A or 420B. Other algorithms can be included to calculate absorption of oxygen in oxyhemoglobin and deoxyhemoglobin, heart arrhythmias, heart rate, premature ventricular contractions, missed beats, systolic and diastolic peaks, large artery stiffness index, In yet other examples, artificial learning or machine learning algorithms can be used in both deterministic and non-deterministic ways to extract information related to a physical condition of a user such as blood pressure and stress levels (from heart rate variability). PPG can also be used to measure blood pressure by computing the pulse wave velocity between two points on the skin separated by a certain distance. Pulse wave velocity is proportional to blood pressure and that relationship can be used to calculate the blood pressure. In some examples, the algorithms can be modified or use information input by a user into memory of electronics 499 such as the user's weight, height, age, cholesterol, genetic information, body fat percentage, or other physical parameter. In other examples, machine learning algorithms can be used to detect and monitor for known or undetected health conditions, such as an arrhythmia, based on information generated by the photodetectors and/or processors.

User interface 494 may be a screen which allows a user to interact with device 400, such as a touch screen or buttons. Display 495 can be an LCD, LED, mobile phone display, electronic ink, or other display to display information about device 400. User interface 494 can allow for both input from a user and output to a user. Communication interface(s) 497 can include hardware and software to enable communication of data over standards such as Wi-Fi, Bluetooth, infrared, radio-wave, and/or other analog and digital communication standards. Communication interface(s) 497 allow for electronics 499 to be updated and information generated by device 400 to be shared to other devices. In some examples, communication interface(s) 497 can send historical information stored in memory 492 to another user device for display, storage, or further analysis. In other examples, communication interface(s) 497 can send the signal generated by the photodetector to another user device in real-time or afterwards for display on that device.

Figure 5:
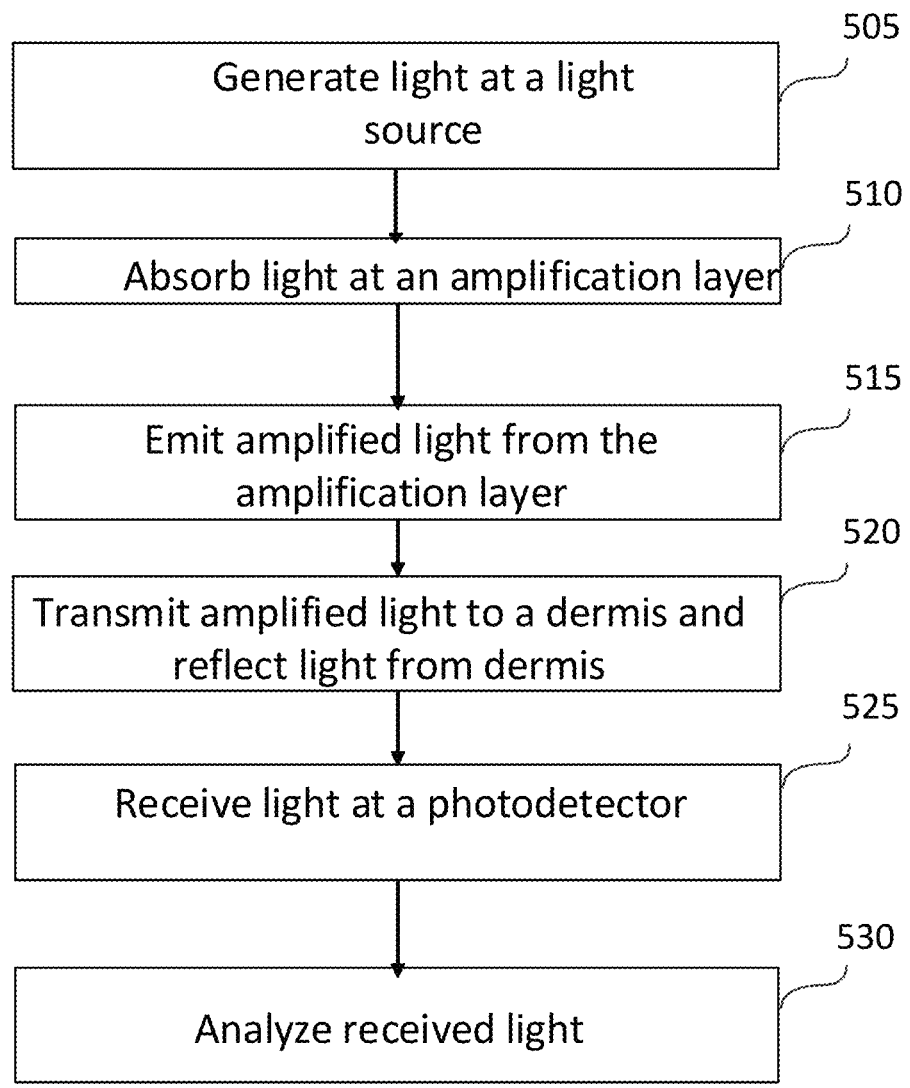
FIG. 5 is a flowchart of an example method according to aspects of this disclosure.

FIG. 5 illustrates a flowchart of an example method 500 of monitoring a physical parameter of a user.

At block 505, a light source can generate light, such as a beam of light or a photon. For example, the light source can be light source 410. The generated light can have a first excitation wavelength, which can correspond to a known excitation wavelength of a rare earth metal. The generated light can be incident on one surface of an amplification layer, such as amplification layer 432. As the process of generating light is energy intensive, producing light of high intensities would require more energy—leading to a device, such as device 400 being bulkier to accommodate a larger power source or having a shorter functional time before requiring recharge. Further, as the wavelengths of light cannot be tightly controlled in a single light source, either light through a larger spectrum of wavelengths would be generated or specialized light sources corresponding to red and green light would be required. As explained further below, the use of a doped glass plate engineered with specific responses to an excitation wavelength can produce green and red light, which in turn can be used to monitor a physical parameter of a user.

At block 510, light generated at block 505 can be absorbed by a photoluminescent material, such as amplification layer 432 or the erbium doped glass plates referenced in FIGS. 1-2. The light received by the photoluminescent material can be amplified by the amplification layer 432. During this process, light with a spectrum of intensities and wavelengths can be generated by the amplification layer 432. The amplification can be several times At block 515, the light generated by the amplification layer 432 can be emitted. The light can be transmitted through one or more sides of the amplification layer. In some examples, the amplification layer can be formed such that light only passes through one surface of the amplification layer.

At block 520, the light can be transmitted to a dermis, such as dermis 450. At block 520, the light can further be reflected from systems and organs within the epidermis, such as vein 460, artery 470, or other capillaries. The amplified light would be incident on the dermis, and a portion of the light would be reflected back from or through the dermis.

At block 525, the light can be detected by a photodetector, such as photodetectors 420A and 420B. The light received can be converted into a digital or analog electrical signal by the photodetectors, and then, transmitted to electronics, such as electronics 499.

At block 530, the received signals, and in turn light received from the photodetector, can be analyzed by electronics, such as electronics 499. With reference to FIG. 4B above, electronics 499 can contain algorithms which can analyze aspects of a user's physical parameter from information which is gleaned through the light received in block 525.

While the method 500 is described below in a particular order, it should be understood that the operations may be performed in a different order or simultaneously. Moreover, operations may be added or omitted.

As described with reference to the disclosure above, the use of a doped photoluminescent material can increase the signal received from a user and reduce the energy requirements of a device to monitor a physical condition of a user. As used within this disclosure, and due the particle/wave duality of light—a beam of light, ray of light, photon, or light, are intended to convey a quantum of light with a wavelength and amplitude, and can be used interchangeably.

While this disclosure contains many specific implementation details, these should not be construed as limitations on the scope of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

References to "or" may be construed as inclusive so that any terms described using "or" may indicate any of a single, more than one, and all of the described terms. The labels "first," "second," "third," and so forth are not necessarily meant to indicate an ordering and are generally used merely to distinguish between like or similar items or elements.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

The invention claimed is:

1. A wearable device comprising:
an amplification configured to receive light of a first wavelength and first intensity on a first surface and transmit light of a second wavelength with a second intensity to a user via a second surface;
a photodetector configured to receive light of the second wavelength incident from skin of the user when the wearable device is in contact with the skin of the user; and
a processor configured to determine a physical condition of the user based on at least a signal received from the photodetector,
wherein:
the first wavelength is an excitation frequency of the amplification layer, and
the second intensity is higher than the first intensity.

2. The wearable device of claim 1, wherein the amplification layer further transmits light of a third wavelength and the photodetector receives light of the third wavelength.

3. The wearable device of claim 2, wherein the processor is further configured to monitor a blood oxygen level based on light of the second wavelength and the processor is configured to monitor a heart condition based on light of a third wavelength.

4. The wearable device of claim 1, wherein the photodetector generates electrical signals responsive to the light received.

5. The wearable device of claim 4, wherein processor is electrically coupled to the photodetector.

6. The wearable device of claim 5, wherein the processor is further configured to evaluate a health state of a user based on received photons of the second wavelength.

7. The wearable device of claim 1, further comprising a paint, which blocks a visible light spectrum, on either the first surface or the second surface of the amplification layer.

8. The wearable device of claim 1, wherein the first wavelength is within an infra-red spectrum.

9. The wearable device of claim 1, wherein the amplification layer is erbium doped phosphate glass.

10. The wearable device of claim 9, wherein the amplification layer is erbium doped phosphate glass with between 0.4 mole percent and 0.6 mole percent of erbium.

11. The wearable device of claim 9, wherein the second wavelength is from a range of 550 to 750 nm wavelength.

12. The wearable device of claim 1, wherein the second wavelength is different than the first wavelength.

13. A method of monitoring a physical parameter of a user, comprising:
providing an amplification layer, the amplification layer configured to have a first excitation wavelength and generate a second excitation wavelength;
generating by a light source light of a first wavelength, the first wavelength corresponding to the first excitation wavelength;
receiving the light of a first wavelength at the amplification layer;
generating light of a second wavelength at the amplification layer responsive to the received light of a first wavelength;
transmitting the light of a second wavelength from the amplification layer to the user;
receiving from the user and at a photodetector, the light of a second wavelength; and
evaluating, by a processor, the physical parameter of the user based on at least the light of a second wavelength received at the photodetector, wherein the physical parameter is at least one of a heart rate or a blood oxygen level of the user.

14. The method of claim 13, further comprising generating light of a third wavelength at the amplification layer.

15. The method of claim 14, wherein the second wavelength corresponds to red light and the third wavelength corresponds to green light.

16. The method of claim 15, wherein evaluation by a processor comprises execution of a machine learning algorithm to evaluate an underlying health condition of the user.

17. A wearable device, comprising:
a housing, the housing comprising a back portion adapted to be placed adjacent to a user's skin;

an amplification layer with a first side and a second side, the amplification layer configured to receive light of a first wavelength and first intensity and transmit light of a second wavelength with a second intensity;

a photodetector configured to receive light of the second wavelength incident from the user's skin when the back portion of the wearable device is placed adjacent to the user's skin; and a processor configured to determine a physical condition of a user based on at least a signal received from the photodetector, wherein:
    the first wavelength is an excitation frequency of the amplification layer, and
    the second intensity is higher than the first intensity.

18. The wearable device of claim 17, wherein the amplification layer is doped with erbium.

19. The wearable device of claim 17, wherein the amplification layer is at least partially painted with an ink to block a visible light spectrum.

20. The wearable device of claim 17, wherein the second wavelength is different than the first wavelength.

* * * * *